(12) United States Patent
Jones et al.

(10) Patent No.: US 6,248,603 B1
(45) Date of Patent: Jun. 19, 2001

(54) METHOD OF MEASURING DIELECTRIC LAYER THICKNESS USING SIMS

(75) Inventors: Clive Martin Jones; Jin Zhao, both of Austin, TX (US)

(73) Assignee: Advanced Micro Devices, Sunnyvale, CA (US)

(*) Notice: Subject to any disclaimer, the term of this patent is extended or adjusted under 35 U.S.C. 154(b) by 0 days.

(21) Appl. No.: 09/615,393

(22) Filed: Jul. 13, 2000

(51) Int. Cl.[7] .................................................. H01L 21/66
(52) U.S. Cl. .......................... 438/14; 438/624; 438/763; 438/712; 324/754
(58) Field of Search ........................ 438/14, 763, 712; 324/754

(56) References Cited

U.S. PATENT DOCUMENTS

| | | | |
|---|---|---|---|
| 6,020,746 | * 2/2000 | Livengood | 324/754 |
| 6,121,060 | * 9/2000 | Kameyama | 438/14 |
| 6,153,537 | * 11/2000 | Bacchetta et al. | 438/763 |
| 6,162,735 | * 12/2000 | Zimmerman et al. | 438/712 |
| 6,174,797 | * 1/2001 | Bao et al. | 438/624 |

FOREIGN PATENT DOCUMENTS

0123456 A2 * 1/2000 (EP) ..................... 100/100

* cited by examiner

*Primary Examiner*—John F. Niebling
*Assistant Examiner*—Olivia Luk
(74) *Attorney, Agent, or Firm*—Crawford PLLC

(57) ABSTRACT

Semiconductor structures having dielectric material layers that are below 3 nanometers in thickness can now be measured with greater precision and in less time using a SIMS device. In an example embodiment of the present invention, a method of measuring the thickness of a dielectric material layer of a semiconductor structure formed on a substrate includes directing a high energy ion beam at a portion of the substrate and sputtering off a plurality of targeted ions from the substrate. The thickness of the dielectric material layer is then determined as a function of a dosage level of the targeted ion and a density of the targeted ion in the dielectric material.

20 Claims, 3 Drawing Sheets

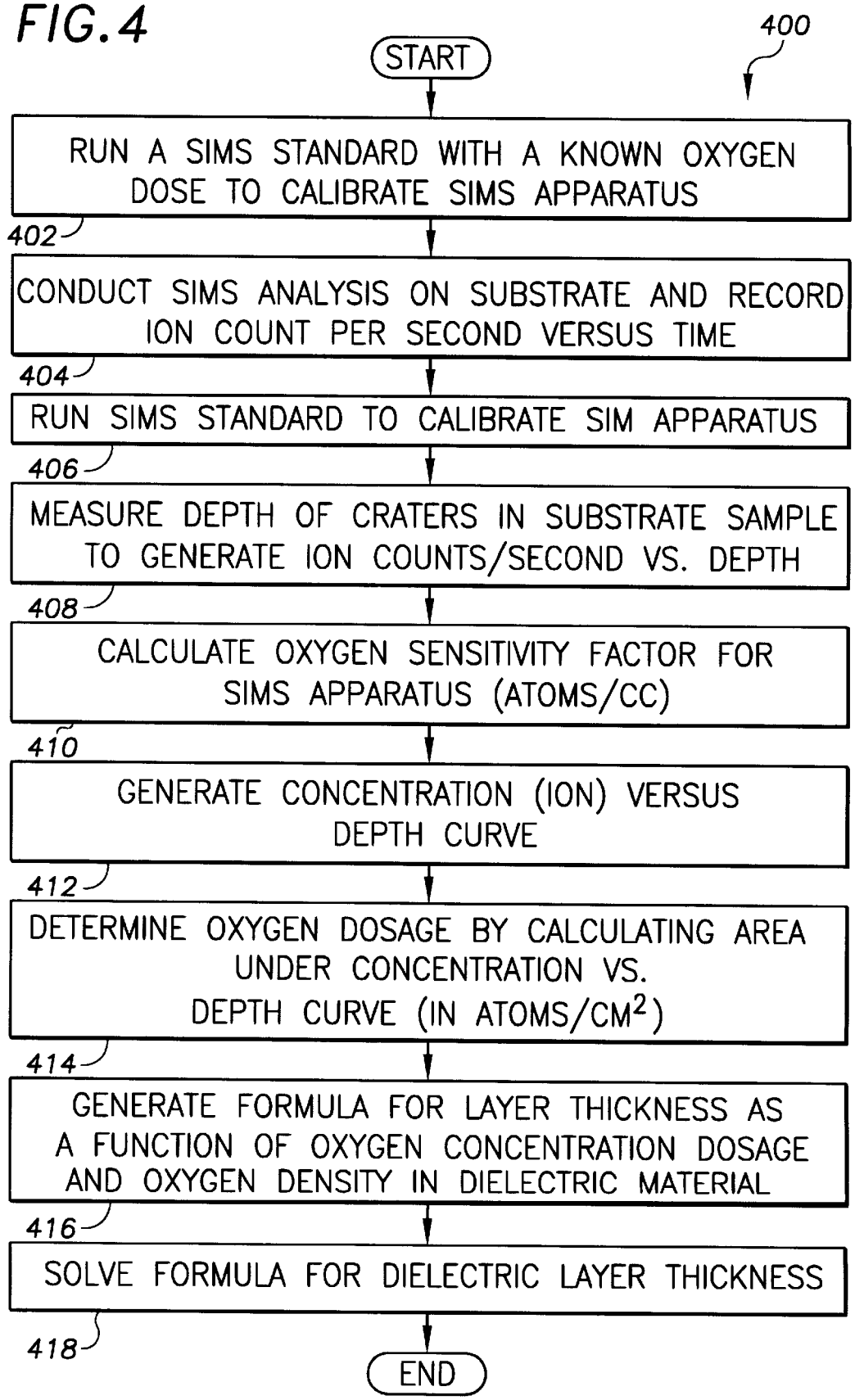

METHOD OF MEASURING DIELECTRIC LAYER THICKNESS USING SIMS

FIELD OF THE INVENTION

The present invention relates generally to semiconductor chips and their fabrication and, more particularly to improving the speed and accuracy of measuring dielectric layers within a semiconductor device or structure.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages.

Many of these semiconductor devices are now affected by conditions brought about by their small size and density on the substrate. With respect to poly-emitter devices and gate oxide transistors, the thickness of the oxide layer is crucial to the speed and performance of the device. Therefore, measuring the thickness of the oxide or dielectric layers on a regular basis is important in monitoring the performance of the wafer processing line. In addition, due to wafer processing anomalies an interfacial oxide layer is sometimes formed through oxidation between the silicon substrate and a polycrystalline layer being deposited on the substrate. This increases the effective thickness of the dielectric layer of the transistor, which affects the device's speed and performance. Even though TEM (transmission electron microscopy) is currently the tool of choice to image cross sections of the thin oxide layers, lengthy sample preparation time required by TEM as well increasingly lower levels of resolution achieved by TEM (as oxide layer thickness decrease by virtue of current wafer processing techniques) is quickly forcing chip designers to look for other alternatives in measuring dielectric layers in integrated circuit devices.

SUMMARY OF THE INVENTION

The present invention is directed to addressing the above and other needs in connection with improving the ability to analyze and measure semiconductor dielectric layers and their thickness using SIMS (Secondary Ions Mass Spectrometry). The thickness regimes for poly-emitter devices (0.1 nm) and for thin gate oxide transistors (1.5 nm–2.5 nm) are too thin to allow for accurate measurement by electron microscopic techniques. It has been discovered that SIMS could be used to determine interlayer silicon dioxide thickness as well as small differences in thickness from wafer to wafer (or across a single wafer) with greater precision than currently available techniques.

According to one aspect of the invention, a method of measuring the thickness of a dielectric material layer of a semiconductor structure formed on a substrate includes directing a high energy ion beam at a portion of the substrate and sputtering off a plurality of targeted ions from the substrate. The thickness of the dielectric material layer is then determined as a function of a dosage level of the targeted ion and a density of the targeted ion in the dielectric material. In a related embodiment, the method further includes detecting a concentration level of the targeted sputtered ions as they are sputtered off the substrate as well as determining a targeted ion concentration level as a function of the depth of an aperture formed in the dielectric material layer by the ion beam.

According to another aspect of the invention, a system for measuring the thickness of a dielectric material layer of a semiconductor structure formed on a substrate includes a high energy ion beam arrangement directed at a portion of the substrate that sputters off a plurality of targeted ions from the substrate. The system further includes an arrangement for determining the thickness of the dielectric material layer as a function of a dosage level of the targeted ion and a density of the targeted ion in the dielectric material. In a related embodiment, the system further includes an arrangement for determining the targeted ion dosage and for determining the density of the targeted ion in the dielectric material. In addition, the system includes an arrangement for correlating the targeted ion dosage and targeted ion density to arrive at the thickness of the dielectric material layer.

According to yet another aspect of the invention, a method and system for calibrating at least a portion of a wafer processing line, the wafer processing line having at least one processing location and at least one processing parameter, includes measuring a dielectric material layer of a semiconductor structure formed on a substrate. The method further includes directing a high-energy ion beam at a portion of the substrate and sputtering off a plurality of targeted ions from the substrate. The thickness of the dielectric material layer is then determined as a function of a dosage level of the targeted ion and a density of the targeted ion in the dielectric material. Finally, the at least one processing parameter is adjusted where it is determined that the dielectric material layer thickness is not within a predefined thickness range.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 4 is a flowchart illustrating the method of measuring an oxide layer in accordance with an embodiment of the invention.

Figure 1:
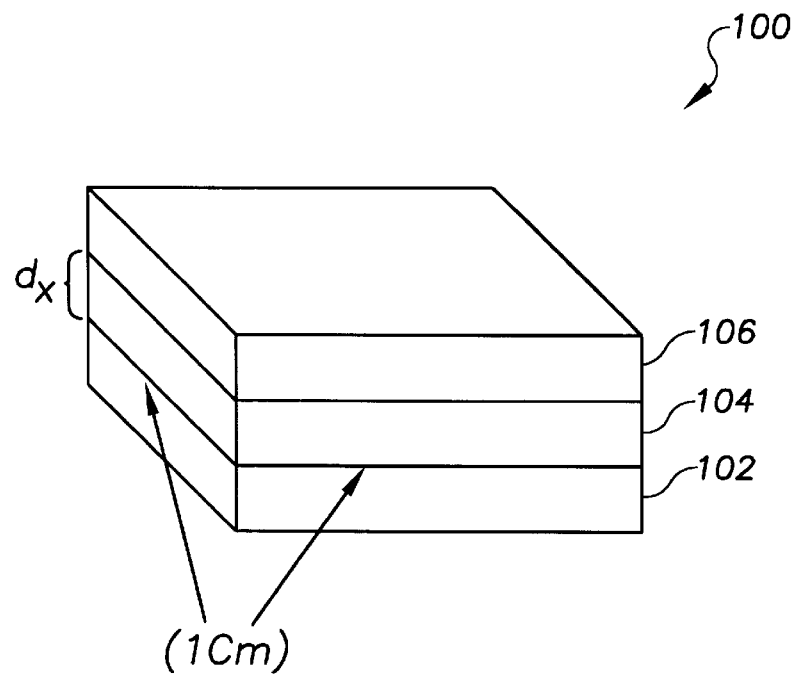
FIG. 1 is an example semiconductor structure that is to be analyzed in accordance with an embodiment of the invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a method and a system for using SIMS to measure dielectric material layers that are about 2–3 nanometers or less in thickness. While the present invention is not necessarily limited to a semiconductor structure processing application and related devices, the invention will be better appreciated using a discussion of exemplary embodiments in such a specific context.

According to an example embodiment of the invention, method of measuring the thickness of a dielectric material layer of a semiconductor structure formed on a substrate includes directing a high energy cesium ion beam from a SIMS device at a polysilicon layer on a silicon substrate and sputtering off a plurality of silicon ions while the SIMS device reaches a steady state condition. After sputtering off several hundred angstroms of polysilicon and after the SIMS device reaches the steady state condition, oxygen ions begin to be sputtered off from the substrate from an interfacial oxide layer formed between the polysilicon layer and the silicon substrate. A concentration level of the oxygen ions as they are sputtered off the substrate is first determined. The concentration level of the oxygen ions as a function of the depth of an aperture formed in the interfacial oxide layer by the ion beam is then determined. The thickness of the interfacial oxide layer is then determined as a function of a dosage level of the oxygen ion and a density of the oxygen ion in the interfacial oxide material.

FIG. 1 illustrates a semiconductor structure 100 composed of a substrate 102, a dielectric material layer 104 and another semiconductor material layer 106. In this example, the substrate is made from silicon and layer 106 is a polycrystalline silicon layer (hereinafter polysilicon), a few hundred nanometers in thickness, that is formed over silicon substrate 102. Through oxidation, an interfacial oxide layer 104 composed of silicon dioxide is formed during deposition of the polysilicon layer. In a related embodiment, the dielectric layer is deliberately formed with silicon dioxide, silicon nitride or any other dielectric material.

In an example embodiment of measuring the thickness of dielectric layer 104, the thickness will be designated as dx and the other two sides of layer 104 will measure about 1 cm. In this example, the density of oxygen in silicon dioxide is calculated as follows:

Density of oxide $(SiO_2) = 7.05 \times 10^{22}$ atoms/cm$^3$

Density of $O_2$ in $SiO_2 = \frac{2}{3} \times 7.05 \times 10^{22}$ atoms/cm$^3 = 4.7 \times 10^{22}$ At/cm$^3$ Therefore 1 square cm of interfacial oxide having dx cm thickness has $N_{ox}$ atoms of oxygen:

\# of atoms=volume x atom density, which in turn equals the # of oxygen atoms in this volume:

$N_{ox} = (4.7 \times 10^2)dx$.

If we know $N_{ox}$, the oxide thickness dx is:

$N_{ox}/(4.7 \times 10^{22})$ cm or $N_{ox}/(4.7 \times 10^{14})$ angstroms.

Therefore, in order to determine the oxide layer thickness in this example the number of oxygen atoms or oxygen dosage needs to be determined as the remaining unknown. The present invention uses SIMS to determine the oxygen dosage in the oxide layer as follows.

The SIMS technique typically uses an ion beam (usually oxygen or cesium) to sputter away layers of a doped region. The sputtered dopant region produces ions that can then be mass analyzed. The sputtered ions are collected by a mass spectrometer for mass to charge separation and detection. The number of ions collected can also be digitally counted to produce quantitative data on the sample composition. SIMS primarily analyzes the material removed by sputtering from a sample surface. By monitoring the secondary ion signals with time, a depth profile can be produced. Typical sputter rates of 2–5 Å per second, at data acquisition time intervals of 0.5–10 seconds, produce typical depth increments in the 20–50 Å range. Usually the incident beam is rastered over a small area of the surface to create a hole or aperture with a nearly flat bottom. Mass analysis is only performed on the ionic fraction of sputtered material from the center of the hole.

Most uses of SIMS involve a low energy beam to bombard the substrate in an effort to preserve the integrity of the layer being measured However, the thinner the layer being measure the lower the energy level that is used in an attempt to sputter off ions from the layer being measured without damaging the layer. Eventually, this approach fails since the energy level is so low that there is not enough energy created to generate the sputtered ions. The present invention uses high-energy bombardment in order that spectrometer 208 detects a steady stream of silicon and then detects a large spike of the targeted ion, which in this example is oxygen within the silicon dioxide layer. The higher the energy the broader the Gaussian distribution, which is unlike the traditional SIMS distributions.

Figure 2:
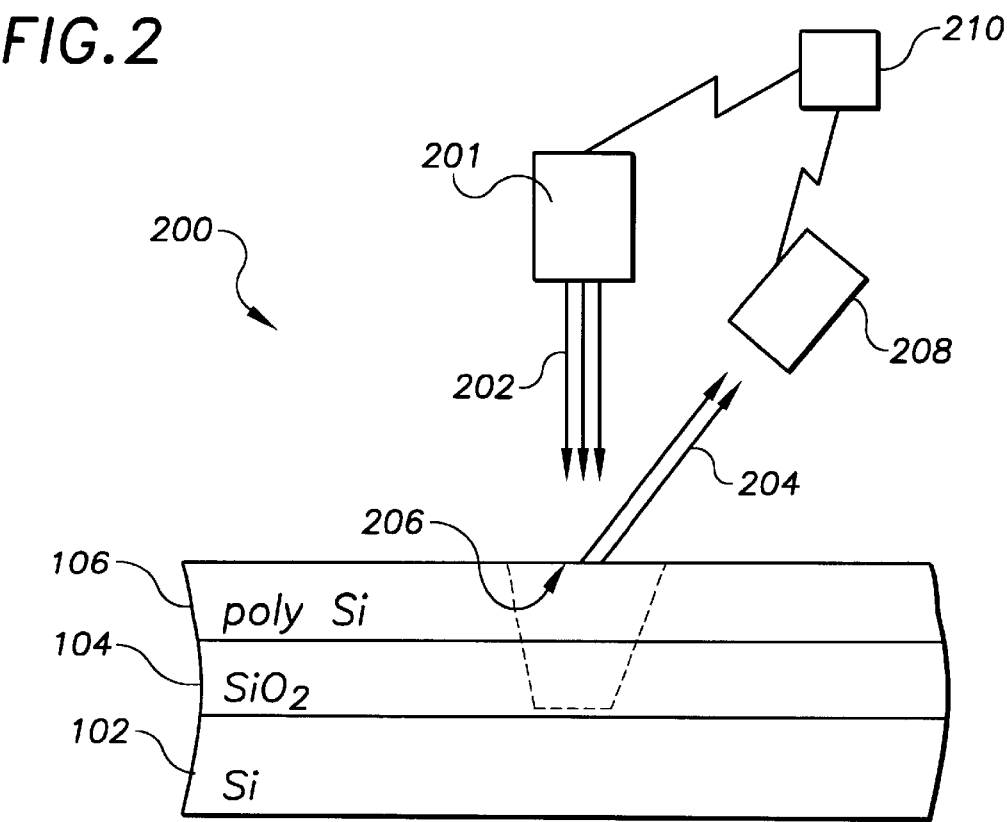
FIG. 2 is the example semiconductor structure of FIG. 1 undergoing SIMS analysis in accordance with an embodiment of the invention.

Referring to FIG. 2 illustrates a system 200 for determining the thickness of dielectric layer 104 of semiconductor structure 100 using a SIMS device. The semiconductor structure 100 includes, for example, poly-emitter devices, thin gate oxide transistors, SOI devices and other similar types of integrated circuits. System 200 positions structure 100 with polysilicon layer 106 facing up and includes a primary focused ion beam (FIB) generating device 201 positioned over polysilicon layer 106 that directs an ion beam 202 at structure 100. Secondary ions 204 in the form of silicon and oxygen are then sputtered off the substrate layers. Ion beam 202 bombards structure 100 with such high energy as to form an aperture (or crater) 206 through polysilicon layer 106 and through silicon dioxide layer 104. Secondary ions 204 are detected by a mass spectrometer 208. The data collected from spectrometer 238 is processed by a computer arrangement 210 coupled to both the spectrometer 208 and to the FIB 201.

Unlike most uses of SIMS for layer thickness calculations, the present ion beam 202 is a high energy beam of about 14.5 KeV (that can go as high as 30 KeV) that bombards structure 100 with cesium (Cs) ions. Other elements can be used as bombardment agents depending on the energy level used and the substrate material to be detected by the ion detector and computer arrangement. The high energy beam causes the thin oxide layer to be diluted by ion beam mixing and the 14.5 KeV net impact energy provides sufficient mixing to change the composition of the interface layer from that of stoichiometric silicon dioxide to silicon with a high dose of oxygen. The areal density of the interfacial oxygen peak is then calibrated against a SIMS oxygen ion implant standard with a precision of better than 3%. The oxide thickness is then calculated with equal precision using the formula derived earlier in the specification.

In the example embodiment described above, it is preferable to have the polysilicon layer with a thickness of 1000 angstroms, but is operable to a thickness of about 200 angstroms. The SIMS device usually requires to be operating for sometime before reaching steady state and properly bombarding structure 100 (during this time the SIMS device initially does generate cesium ions for bombardment, but the sputtering rate and secondary ion yields take a finite time to reach equilibrium). Therefore, a certain thickness of polysilicon is required on the substrate before the primary ion beam with the cesium ion reaches the oxide layer to be measured. In a related embodiment, the non-dielectric material layer above the dielectric layer to be measured, such as the gate electrode layer over a thin oxide layer in a transistor, needs to be thick enough to manage the steady state operating condition of the SIMS device.

Figure 3:
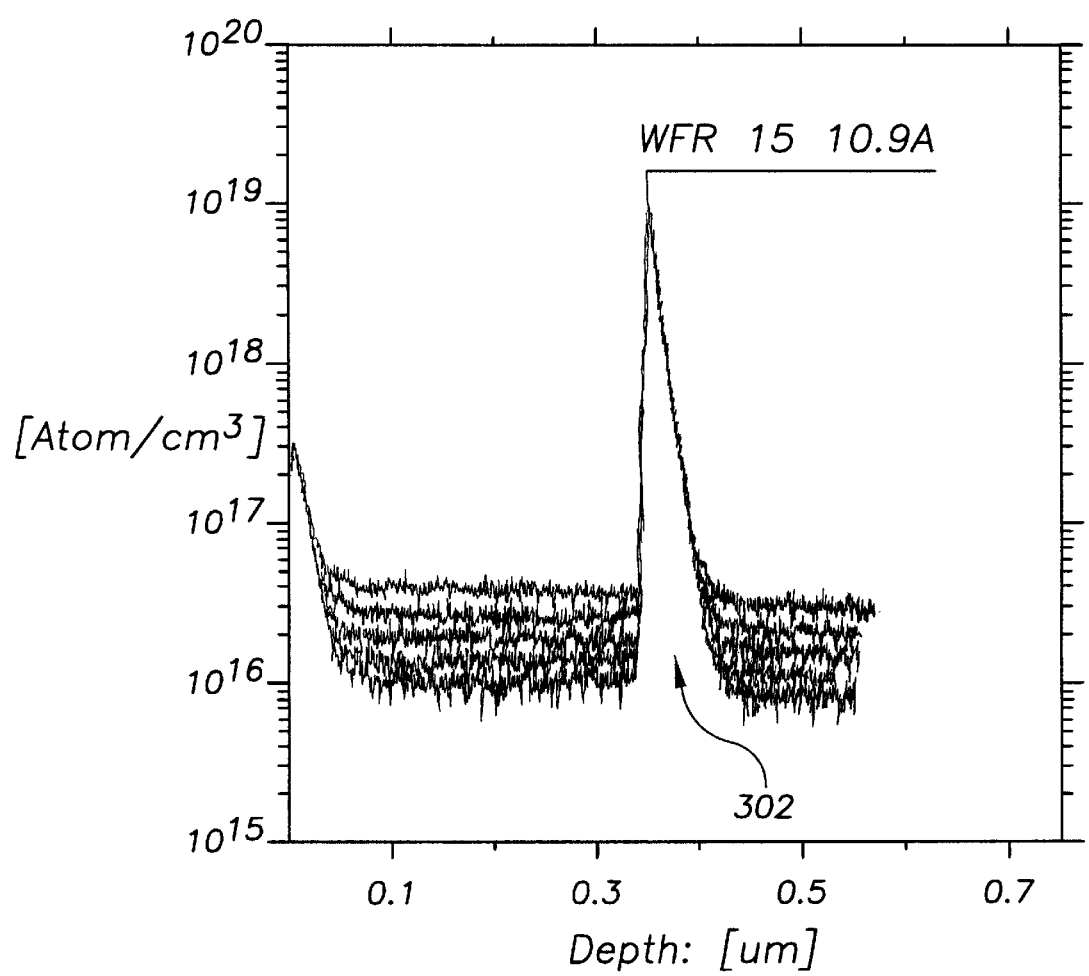
FIG. 3 is an pie graph showing SIMS depth profile exhibiting ion concentration versus silicon thickness in accordance with an embodiment of the invention.

Referring now to FIG. 3, graph 300 illustrates a concentration versus depth graph generated by the SIMS system 200. An ideal profile (not shown) of an interfacial oxide concentration versus depth graph would reflect a horizontal line indicating that only silicon is detected, then a column indicating the spike in oxygen from the silicon dioxide layer, and back to a horizontal line indicating that only silicon is detected as reflected by the layers of structure 100 (see FIG. 1). However, since the polysilicon/silicon oxide/silicon interfaces are made diffuse by the high-energy bombardment they generate the type of curve illustrated in FIG. 3. The high energy bombardment also overcomes the SIMS matrix effect (wherein the ion yield varies depending on the type of base material that the targeted ion is in) and provides the opportunity to use critical dose matching procedures to calculate the dose of oxygen (area under curve 300 indicated as 302) since the oxygen distribution is similar to a standard ion implant profile for oxygen. The number of atoms of oxygen can now be calculated when the distribution is compared with standard oxygen ion implant profiles.

SIMS is one of the few surface analysis techniques that can measure ion level concentrations in electronic materials, and therefore is particularly useful for detecting the different ion levels as interfaces in the substrate are crossed. However, it is recognized that SIMS does not possess sufficient resolution capabilities with respect to depth when attempting to accurately profile through an oxide layer having a thickness less then 30 angstroms. Therefore, contrary to the traditional thinking it has been discovered that instead of using a low energy primary beam to improve depth resolution, a high energy beam be used to promote ion beam mixing and dilute the interfacial oxide. In this manner, the analysis moves in the direction of becoming a distribution similar to an ion implant profile and then becomes a dose matching exercise as described above. In a related embodiment, invention is capable of measuring nitride based dielectric materials or other non-dielectric materials where the targeted ion can be detected and measured and standard ion profiles are available.

Referring to FIG. 4, a flowchart 400 illustrates an example implementation of the method of measuring a dielectric material layer in a semiconductor device or structure. At 402, a SIMS ion implant standard is run with a known oxygen dose to calibrate the SIMS apparatus. At 404, SIMS analysis is conducted on structure 100, as in FIG. 2, and the oxygen ion count per second versus time is detected and recorded. The time ranges from 0.5 to 1 second, with various data points being taken. At 406, another SIMS ion implant standard is run with a known oxygen dose to again calibrate the SIMS apparatus. At 408, the depth of the apertures or craters is measured with a stylus profilometer to help generate an oxygen ion count per second versus depth profile. At 410, the oxygen sensitivity factor (in atoms/cm$^3$) for the SIMS device is calculated from the data gathered during the two calibration runs at 402 and 406.

At 412, a concentration versus depth curve (for oxygen ion) is then generated from the sensitivity factor and the crater measurements (in atoms/cm$^3$ versus depth). At 414, the oxygen dosage is determined by calculating the area under the concentration/depth curve. In essence, the various data points comprise a plurality of histograms, each representing sputtered depth traversed (in centimeters), each multiplied by the height of the histogram (concentration—atoms/cm$^3$) and multiplied by all of the data points. The end result is the oxygen dosage in atoms/cm$^2$. At 416, the formula is generated for determining the dielectric material layer thickness (see discussion before FIG. 2) as a function of oxygen dosage/concentration and as a function of oxygen density in the dielectric material used in the dielectric layer. At 418, the formula for dielectric layer thickness is solved as follows:

Oxide thickness in Angstroms=(SIMS oxygen dose/14.7×10$^{14}$).

In a related embodiment, the method described herein is used in a system for calibrating at least a portion of a wafer processing line, the wafer processing line having at least one processing location and at least one processing parameter. The wafer processing line is calibrated by measuring a dielectric material layer of a semiconductor structure on a substrate formed by the processing line. A high-energy ion beam is first directed at a portion of the substrate to sputter off a plurality of targeted ions from the substrate. The thickness of the dielectric material layer is then determined as a function of a dosage level of the targeted ion and a density of the targeted ion in the dielectric material. Finally, the at least one processing parameter is adjusted where it is determined that the dielectric material layer thickness is not within a predefined thickness range. In this example, the chamber that deposits the dielectric layer has the processing parameters adjusted to ensure that the dielectric layer is deposited to the proper thickness on the following substrate. In a related example, the chamber that deposits a polysilicon layer on a silicon substrate has the vacuum adjusted in order to lower the possibility of oxidation that occurs within the chamber and increases the thickness of the interfacial oxide layer.

The method described herein is superior, in several ways, to the current TEM (transmission electron microscopy) methods used to image cross sections of thin oxide interlayers. Firstly, the SIMS approach is more accurate in where the layers have a thickness below 1.5 nm range while the thickness measurement using TEM becomes increasingly less accurate going from 1.5 nm to 1 nm and cannot accurately measure layers less than 1 nm in thickness. Secondly, the aforementioned method gives a statistical average of the film thickness over a 30 micron range, whereas a TEM cross section traverses only about 100 nm range and may not give a representative answer without making numerous analyses which can be extremely time consuming. Finally, the aforementioned method requires no sample preparation aside from cleaning and can be completed within hours; whereas the TEM preparation and analysis takes substantially more time.

While the present invention has been described with reference to several particular example embodiments, those skilled in the art will recognize that many changes may be made thereto without departing from the spirit and scope of the present invention, which is set forth in the following claims.

What is claimed is:

1. A method of measuring the thickness of a dielectric material layer of a semiconductor structure formed on a substrate, the method comprising:

directing a high energy ion beam at a portion of the substrate and sputtering off a plurality of targeted ions from the substrate; and determining the thickness of the dielectric material layer as a function of a dosage level of the targeted ion and a density of the targeted ion in the dielectric material.

2. The method of claim 1, before the step of directing a high energy ion beam, further including the step of forming a non-dielectric material layer on the dielectric layer.

3. The method of claim 2, wherein the step of forming a non-dielectric material layer includes forming non-dielectric layer from a polycrystalline silicon material.

4. The method of claim 2, further including the step of forming the non-dielectric material layer to a thickness of about 200 angstroms or greater.

5. The method of claim 2, further including the step of forming the dielectric material from an oxide material and selecting oxygen as the targeted ion.

6. The method of claim 2, further including the step of forming the dielectric material from a nitride material and selecting nitrogen as the targeted ion.

7. The method of claim 3, wherein the step of directing a high-energy ion beam includes using a SIMS device.

8. The method of claim 7, wherein the ion beam is comprised of a 14.5 KeV beam of cesium ions.

9. The method of claim 8, wherein the step of determining the thickness of the dielectric material further includes the steps of:

generating a targeted ion concentration versus depth curve profile; and determining the targeted ion dosage by calculating the area under the concentration versus depth curve.

10. The method of claim 9, further including the steps of:

determining the density of the targeted ion in the dielectric material; and correlating the targeted ion dosage and targeted ion density to arrive at the thickness of the dielectric material layer.

11. A method for measuring the thickness of a dielectric material layer of a semiconductor structure formed on a substrate, the method comprising the steps of:

directing a high-energy ion beam at the substrate and sputtering off a plurality of targeted ions from the substrate;

detecting a concentration level of the targeted sputtered ions as they are sputtered off the substrate;

determining a targeted ion concentration level as a function of the depth of an aperture formed in the dielectric material layer by the ion beam; and determining the thickness of the dielectric material layer as a function of a dosage level of the targeted ion and a density of the targeted ion in the dielectric material.

12. The method of claim 11, before the step of directing a high energy ion beam, further including the step of forming a non-dielectric material layer on the dielectric layer to a thickness of about 200 angstroms or greater.

13. The method of claim 12, further including the step of forming the dielectric material from an oxide material and selecting oxygen as the targeted ion.

14. The method of claim 13, wherein the ion beam is comprised of a 14.5 KeV beam of cesium ions generated by a primary beam of a SIMS device.

15. The method of claim 14, wherein the step of determining the thickness of the dielectric material further includes the steps of:

generating a targeted ion concentration versus depth curve profile; and determining the targeted ion dosage by calculating the area under the concentration versus depth curve.

16. The method of claim 15, wherein further including the steps of:

determining the density of the targeted ion in the dielectric material; and correlating the targeted ion dosage and targeted ion density to arrive at the thickness of the dielectric material layer.

17. A system for measuring the thickness of a dielectric material layer of a semiconductor structure formed on a substrate, the system comprising:

means for directing a high energy ion beam at a portion of the substrate and sputtering off a plurality of targeted ions from the substrate; and means for determining the thickness of the dielectric material layer as a function of a dosage level of the targeted ion and a density of the targeted ion in the dielectric material.

18. The system of claim 17, wherein the system further includes:

means for generating a targeted ion concentration versus depth curve profile;

means for determining the targeted ion dosage by calculating the area under the concentration versus depth curve;

means for determining the density of the targeted ion in the dielectric material; and means for correlating the targeted ion dosage and targeted ion density to arrive at the thickness of the dielectric material layer.

19. A system for calibrating at least a portion of a wafer processing line by measuring a dielectric material layer of a semiconductor structure formed on a substrate, the wafer processing line having at least one processing location and at least one processing parameter, the method comprising:

means for directing a high-energy ion beam at a portion of the substrate and sputtering off a plurality of targeted ions from the substrate;

means for determining the thickness of the dielectric material layer as a function of a dosage level of the targeted ion and a density of the targeted ion in the dielectric material; and means for adjusting the at least one processing parameter where it is determined that the dielectric material layer thickness is not within a predefined thickness range.

20. A method of calibrating at least a portion of a wafer processing line by measuring a dielectric material layer of a semiconductor structure formed on a substrate, the wafer processing line having at least one processing location and at least one processing parameter, the method comprising:

directing a high-energy ion beam at a portion of the substrate and sputtering off a plurality of targeted ions from the substrate;

determining the thickness of the dielectric material layer as a function of a dosage level of the targeted ion and a density of the targeted ion in the dielectric material; and adjusting the at least one processing parameter where it is determined that the dielectric material layer thickness is not within a predefined thickness range.

* * * * *

UNITED STATES PATENT AND TRADEMARK OFFICE
CERTIFICATE OF CORRECTION

PATENT NO.     : 6,248,603 B1
DATED          : June 19, 2001
INVENTOR(S)    : Jones et al.

It is certified that error appears in the above-identified patent and that said Letters Patent is hereby corrected as shown below:

Column 1,
Line 38, "decrease" should read -- decreases --.

Column 2,
Line 53, "an pie graph" should read -- an example --.

Column 3,
Line 11, before "method" please insert "a."

Column 4,
Line 19, "measure" should read -- measured --.

Column 5,
Line 41, after "thinking" please insert -- ,. --

Signed and Sealed this

Ninth Day of July, 2002

Attest:

Attesting Officer

JAMES E. ROGAN
Director of the United States Patent and Trademark Office